(12) United States Patent
Higuchi

(10) Patent No.: US 10,813,540 B2
(45) Date of Patent: Oct. 27, 2020

(54) MEDICAL TUBE AND MEDICAL SYSTEM

(71) Applicant: OLYMPUS CORPORATION, Tokyo (JP)

(72) Inventor: Tatsuya Higuchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 327 days.

(21) Appl. No.: 15/815,126

(22) Filed: Nov. 16, 2017

(65) Prior Publication Data

US 2018/0132705 A1 May 17, 2018

Related U.S. Application Data

(63) Continuation of application No. PCT/JP2016/065362, filed on May 24, 2016.

(30) Foreign Application Priority Data

May 25, 2015 (JP) .................................. 2015-105609

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00059* (2013.01); *A61B 1/00133* (2013.01);
(Continued)

(58) Field of Classification Search
CPC ... A61B 1/018; A61B 1/00135; A61B 1/0059; A61B 1/00137; A61B 1/00133;
(Continued)

(56) References Cited

U.S. PATENT DOCUMENTS 5,025,778 A 6/1991 Silverstein et al.
5,540,668 A * 7/1996 Wilson, Jr. .......... A61M 39/223
604/248

(Continued)

FOREIGN PATENT DOCUMENTS

EP 2 394 564 A1 12/2011
JP 2000-507119 A 6/2000
(Continued)

OTHER PUBLICATIONS

International Search Report dated Aug. 16, 2016 received in PCT/JP2016/065362.
(Continued)

*Primary Examiner* — Aaron B Fairchild
(74) *Attorney, Agent, or Firm* — Scully, Scott, Murphy & Presser, P.C.

(57) ABSTRACT

Provided is a medical tube including: a main body; a first lumen formed in the main body in a longitudinal direction of the main body; a plurality of second lumens formed in the main body in the longitudinal direction of the main body, the plurality of second lumens formed about at least a portion of a circumference of the first lumen; a portion of a distal end of the first lumen comprising a first indicator, the first indicator configured to specify a rotational direction position about the longitudinal direction of the main body of any one of the plurality of second lumens with respect to the first lumen; and a portion of the proximal end of the main body comprising a plurality of second indicators, wherein each of the plurality of second indicators are configured to indicate each of the plurality of second lumens specified by the first indicator.

11 Claims, 8 Drawing Sheets

(51) Int. Cl.
*A61M 39/10* (2006.01)
*A61M 39/08* (2006.01)

(52) U.S. Cl.
CPC ...... *A61B 1/00135* (2013.01); *A61B 1/00137* (2013.01); *A61B 1/0005* (2013.01); *A61B 1/00009* (2013.01); *A61M 39/105* (2013.01); *A61M 2039/082* (2013.01)

(58) Field of Classification Search
CPC ............ A61B 1/00009; A61B 1/0005; A61M 39/105; A61M 2039/082
See application file for complete search history.

(56) References Cited

U.S. PATENT DOCUMENTS

| | | |
|---|---|---|
| 5,749,889 A | 5/1998 | Bacich et al. |
| 5,772,628 A | 6/1998 | Bacich et al. |
| 5,810,776 A | 9/1998 | Bacich et al. |
| 2004/0116920 A1* | 6/2004 | Rioux ................ A61B 18/1492 606/41 |
| 2006/0235457 A1 | 10/2006 | Belson |
| 2006/0235458 A1 | 10/2006 | Belson |
| 2010/0063358 A1 | 3/2010 | Kessler |
| 2011/0004060 A1 | 1/2011 | Honda et al. |
| 2011/0315147 A1 | 12/2011 | Wood et al. |

FOREIGN PATENT DOCUMENTS

| | | |
|---|---|---|
| JP | 2001-299684 A | 10/2001 |
| JP | 2008-538709 A | 11/2008 |
| JP | 2013-172780 A | 9/2013 |
| WO | 91/14391 A2 | 10/1991 |
| WO | 97/29680 A1 | 8/1997 |
| WO | 2006/113544 A2 | 10/2006 |
| WO | 2010/089923 A1 | 8/2010 |
| WO | 2012/005850 A1 | 1/2012 |
| WO | 2013/144914 A2 | 10/2013 |

OTHER PUBLICATIONS

Extended Supplementary European Search Report dated Jan. 9, 2019 received in European Patent Application No. 16 80 0029.7.

\* cited by examiner

MEDICAL TUBE AND MEDICAL SYSTEM

CROSS-REFERENCE TO RELATED APPLICATIONS

This is a continuation of International Application PCT/JP2016/065362, with an international filing date of May 24, 2016, which is hereby incorporated by reference herein in its entirety.

This application is based on Japanese Patent Application No. 2015-105609 filed on May 25, 2015, the contents of which are incorporated herein by reference.

TECHNICAL FIELD

The present invention relates to a medical tube and a medical system.

BACKGROUND ART

There is a known tube provided with a plurality of lumens into which an endoscope and a treatment tool are inserted.

A lumen that can be expanded in order to ensure a large enough channel for inserting a treatment tool or the like while making the tube diameter small during insertion.

An aspect of the present invention is a medical tube including: a first lumen that forms an endoscope channel by penetrating through a tube main body, which is constituted of a material possessing flexibility, in a longitudinal-axis direction; a plurality of second lumens that are capable of forming treatment-tool channels by penetrating through the tube main body in the longitudinal-axis direction at a periphery of the first lumen with spacings therebetween in a circumferential direction; a first indicator that is provided on an inner surface in the vicinity of a distal end of the first lumen and that specifies a circumferential-direction position of any one of the second lumens with respect to the first lumen; and a second indicator that is provided at a proximal end of the tube main body, and that indicates the second lumen specified by the first indicator.

Another aspect of the present invention is a medical system including: any one of the above-described medical tubes; an endoscope that is inserted into the first lumen of the medical tube; a display that displays an image acquired by using the endoscope; an image processor that recognizes the first indicator in the image; and a notifying portion that issues, on the basis of the first indicator recognized by the image processor, a notification about the identification information of one or more of the second lumens specified by the first indicator.

DESCRIPTION OF EMBODIMENT

A medical tube 1 according to an embodiment of the present invention will be described below with reference to the drawings.

In the discussion and claims herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either be completely flat, or so nearly flat that the effect would be the same as if it were completely flat.

Figure 1:
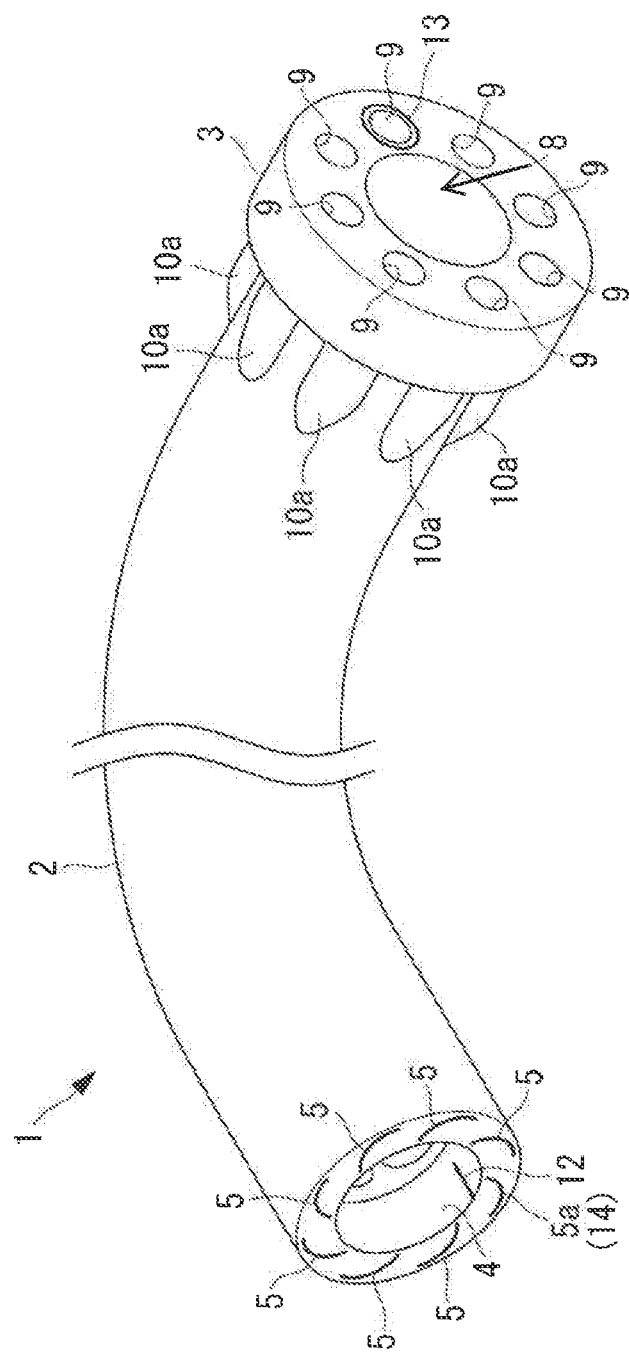
FIG. 1 is a perspective view showing a medical tube according to an embodiment of the present invention.

As shown in FIG. 1, the medical tube 1 according to this embodiment is provided with a tube main body 2 formed of a flexible material, for example, a silicone resin, and a cap member 3 attached to a proximal end of the tube main body 2.

The tube main body 2 is provided with, at substantially the center of a lateral cross-section thereof, a first lumen 4 that passes therethrough in the longitudinal-axis direction, and a plurality of second lumens 5 and 5a that are provided at a periphery of the first lumen 4 with spacings therebetween in the circumferential direction.

The first lumen 4 has a large enough diameter to allow an endoscope (6 of FIG. 4) to be inserted thereinto and forms an endoscope channel. In the state in which a treatment tool (7 of FIG. 2B) is not inserted, the second lumen 5a is collapsed, as shown in FIG. 2A, and, when the treatment tool 7 is inserted, the second lumen 5a is expanded by the treatment tool 7, as shown in FIG. 2B, thus being expanded to a diameter that allows the treatment tool 7 to be inserted thereinto so as to form a treatment-tool channel.

Figure 2A:
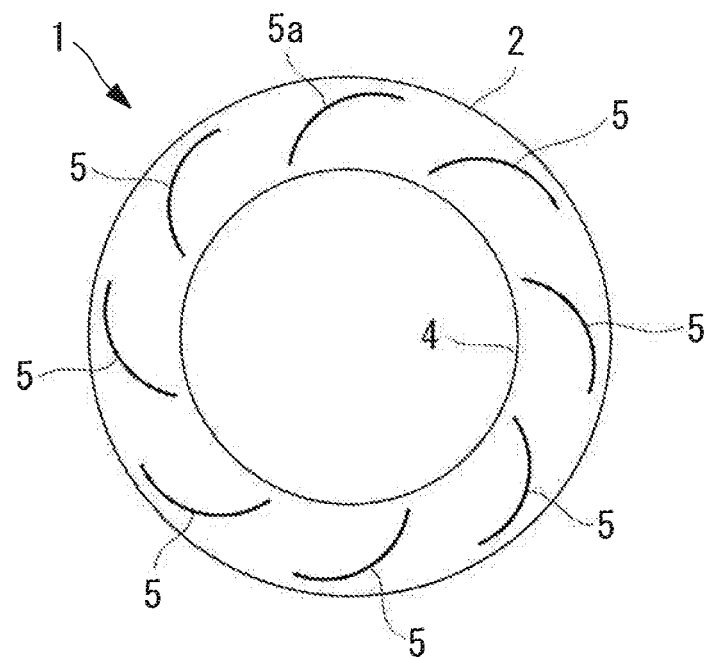
FIG. 2A is a lateral cross-sectional view in which a treatment tool is not inserted into any of second lumens in the medical tube in FIG. 1.
Figure 2B:
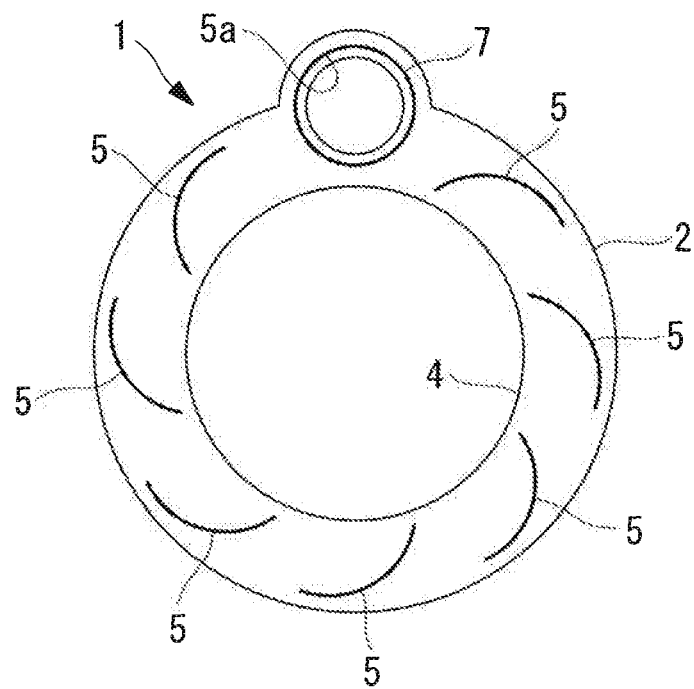
FIG. 2B is a lateral cross-sectional view in which the treatment tool is inserted into one of the second lumens in the medical tube in FIG. 1.

As shown in FIG. 2B, when the second lumens 5 and 5a are expanded, because the outer surface of the tube main body 2 is expanded radially outward, the outer diameter of the tube main body 2 is decreased to a minimum size in the state in which the second lumens 5 and 5a are collapsed, as shown in FIG. 2A.

Figure 3:
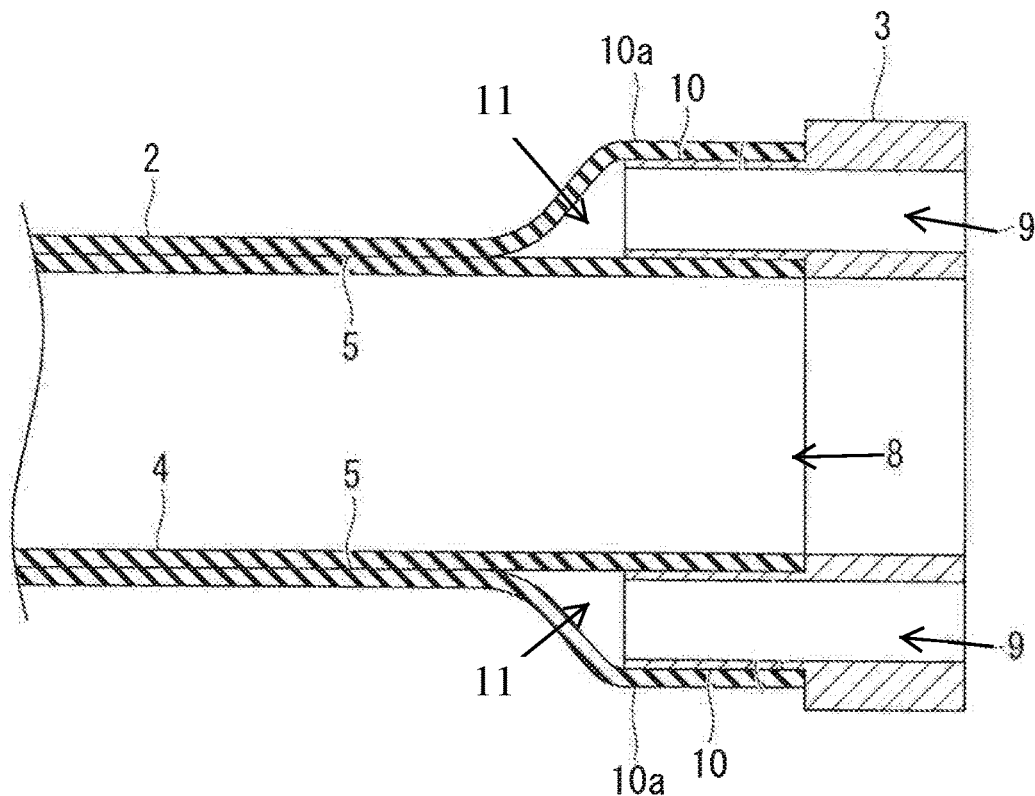
FIG. 3 is a longitudinal cross-sectional view showing a cap member attached to a proximal-end portion of the medical tube in FIG. 1.

As shown in FIG. 3, the cap member 3 is formed in an annular shape having a center through-hole 8 that has a diameter substantially equivalent to that of the first lumen 4 and that is provided at a position substantially aligned with the first lumen 4 in a state in which the cap member 3 is attached to the proximal end of the tube main body 2. At the periphery of the center through-hole 8, as many peripheral through-holes 9 and 9a as there are the second lumens 5 and 5a are provided at positions aligned with the second lumens 5 and 5a.

The peripheral through-holes 9 and 9a each have a large enough diameter to allow the treatment tool 7 to be inserted thereinto. In addition, a plurality of insertion cylindrical portions 10 that extend in an axial direction from positions aligned with the individual peripheral through-holes 9 and 9a are provided at one end of the cap member 3 in the axial direction. As shown in FIG. 3, the cap member 3 is attached to the proximal end of the tube main body 2 by inserting the insertion cylindrical portions 10 by expanding proximal-end openings 11 of the second lumens 5 and 5a (reference sign 10a in FIG. 1 indicates portions of the tube main body 2 that are expanded due to insertion of the insertion cylindrical portions 10 into the second lumens 5).

As shown in FIG. 1, the medical tube 1 according to this embodiment is provided with a distal-end marker (first indicator) 12 that is provided on an inner surface of the first lumen 4 in the vicinity of the distal end of the tube main body 2 and a proximal-end marker (second indicator) 13 that is provided on the cap member 3.

The distal-end marker 12 can be one or more lines that are drawn along the axial direction so as to indicate a specific position in the circumferential direction. The one or more lines of the distal-end marker 12, in FIG. 1 shown as one line, can be straight or have another shape or pattern. This distal-end marker 12 specifies a distal-end position of a single second lumen 5a that exists in the vicinity of the position of the distal-end marker 12.

The proximal-end marker 13 is provided at the position of any one of the peripheral through-holes 9a of the cap member 3 so as to indicate a proximal-end position of the second lumen 5a for which the distal-end position thereof is specified by the distal-end marker 12. In the example shown in FIG. 1, the proximal-end marker 13 is a circular marker that surrounds the peripheral through-hole 9a to be specified.

The operation of the thus-configured medical tube 1 according to this embodiment will be described below.

Figure 4:
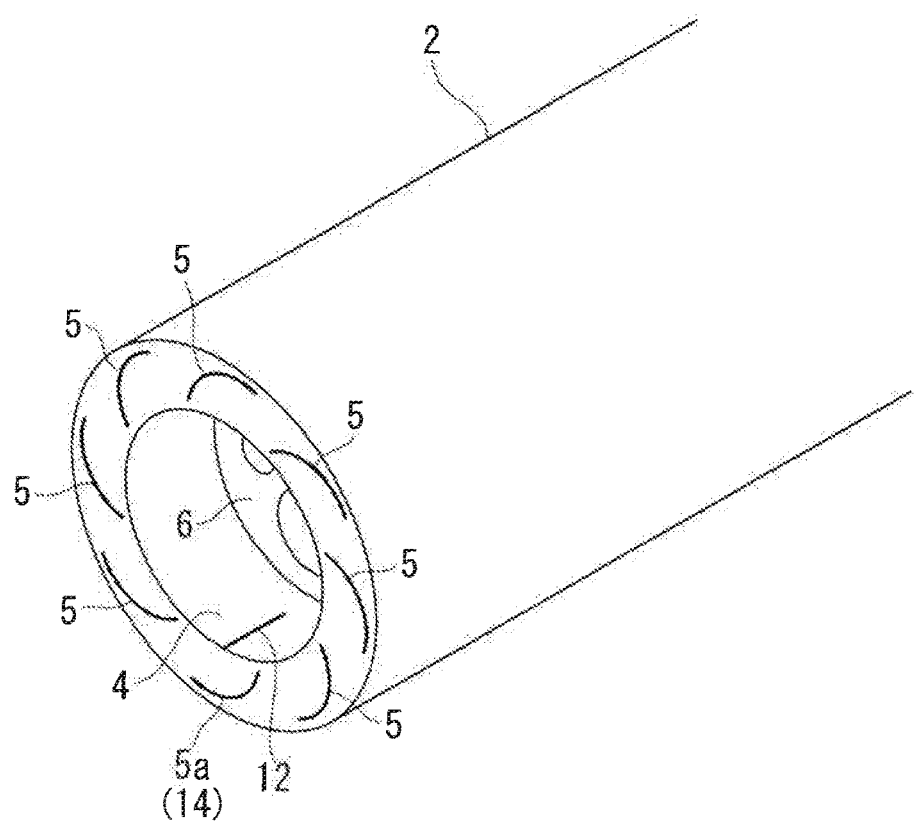
FIG. 4 is a perspective view showing a distal-end portion of the medical tube in FIG. 1 in a state in which an endoscope is inserted into a first lumen.

In order to introduce the endoscope 6 and the treatment tool 7 by using the medical tube 1 according to this embodiment so as to reach an affected portion in the body, the medical tube 1 is inserted into the body of a patient from the distal-end side thereof in a state in which the endoscope 6 is inserted into the first lumen 4 of the medical tube 1. At this time, as shown in FIG. 4, in a state in which the endoscope 6 is slightly retracted into the first lumen 4 from the distal end of the medical tube 1, the endoscope 6 is disposed at a position at which it is possible to acquire an image P that includes an inner surface of the first lumen 4, as shown in FIG. 5.

Because the medical tube 1 is formed of a flexible material and has a small outer diameter in the state in which the treatment tool 7 is not inserted, when inserting the endoscope 6, it is possible to insert the endoscope 6 without substantially hindering bending thereof and, in addition, without exerting a large burden on the patient. However, because the medical tube 1 does not have a relatively high torsional rigidity (as does the endoscope 6), relative distortion sometimes occurs with respect to the endoscope 6 during insertion.

Figure 5:
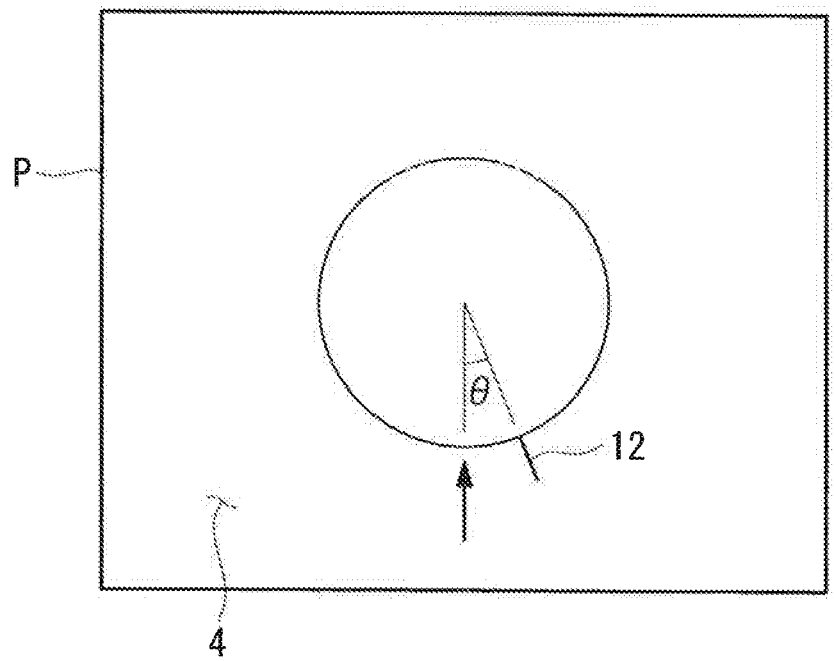
FIG. 5 is a diagram showing an example of an image acquired by using the endoscope inserted into the first lumen in the medical tube in FIG. 1.

In this case, with the medical tube 1 according to this embodiment, because the distal-end marker 12 provided on the inner surface of the first lumen 4 and the proximal-end marker 13 provided on the cap member 3 are provided so as to indicate the distal-end opening 14 and the peripheral through-hole (proximal-end opening) 9a of the same the second lumen 5a and, even if the medical tube 1 is distorted with respect to the endoscope 6, an operator can set, by using the markers 12 and 13 as references, the peripheral through-hole 9a from which the treatment tool 7 can be protruded to a desired position in the image P acquired by the endoscope 6 (as shown in FIG. 5).

In other words, in the image P acquired by using the endoscope 6 (as shown in FIG. 5), the operator checks the position of the distal-end marker 12, and checks the relative position (for example, 45° in clockwise) of the position to which he/she wants to make the treatment tool 7 protrude (for example, position indicated by arrow in FIG. 5) with respect to the distal-end marker 12, and thus, it is possible for the operator to set, as the peripheral through-hole 9a through which the treatment tool 7 is inserted, the peripheral through-hole 9 that is disposed at a position shifted by an amount indicated by the above-described relative position with respect to the proximal-end marker 13 of the cap member 3. Then, after the peripheral through-hole 9a through which the treatment tool 7 is inserted is set, by inserting the treatment tool 7 from the set peripheral through-hole 9a, the operator can make the treatment tool 7 protrude at the desired position just by inserting the treatment tool 7 into the second lumen 5a by expanding the second lumen 5a connected to said peripheral through-hole 9a.

In other words, with the medical tube 1 according to this embodiment, even if the medical tube 1 is distorted with respect to the endoscope 6, it is not necessary to apply torque to the medical tube 1 or to temporarily remove the medical tube 1 from the body to fix the distortion and then to re-insert the medical tube 1, and thus, there is an advantage in that it is possible to reduce the burden exerted on the patient.

Figure 6:
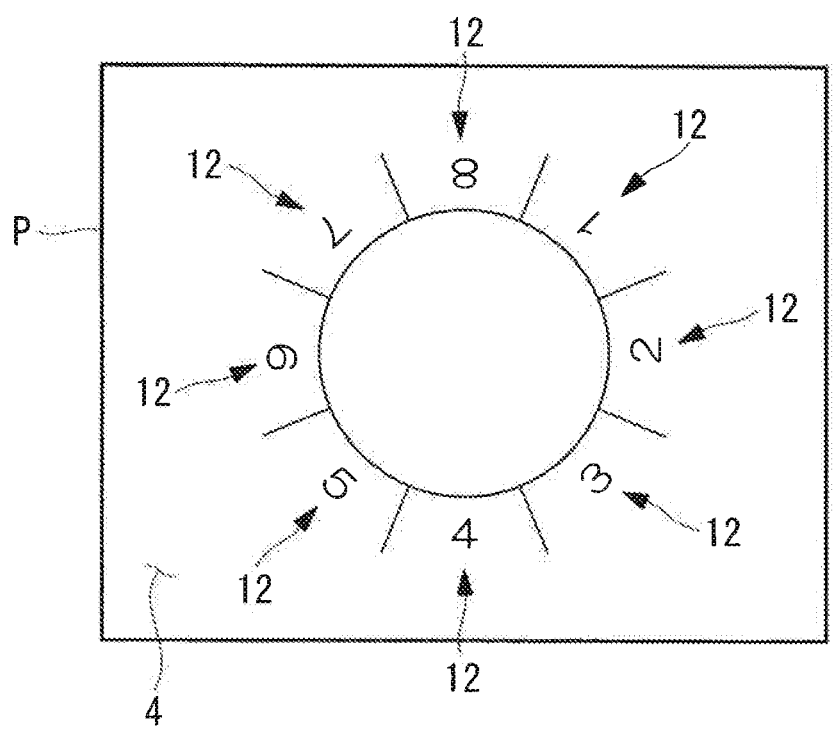
FIG. 6 is a diagram showing an example of an image that includes a modification of a distal-end marker of the medical tube in FIG. 1.
Figure 7:
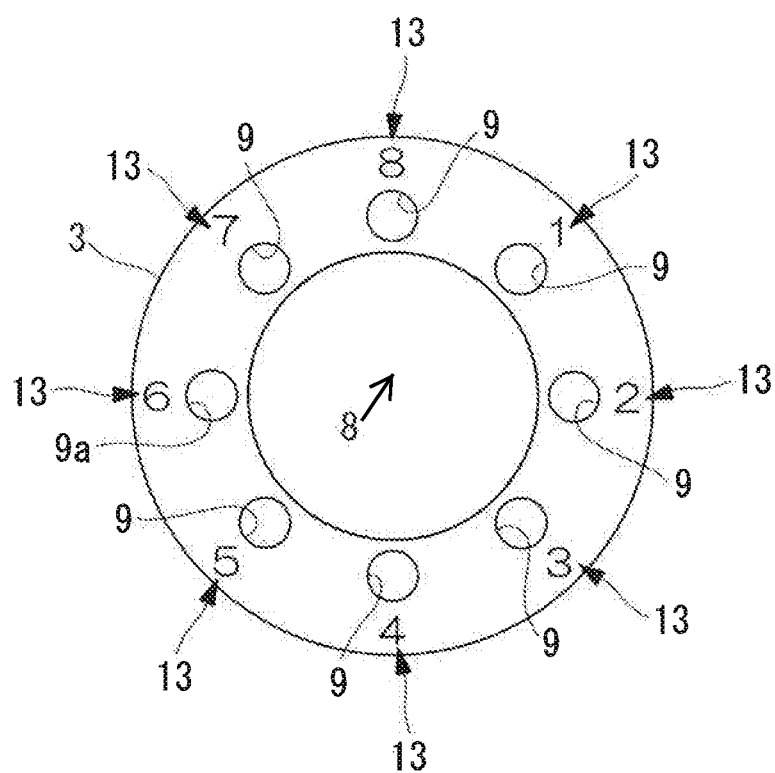
FIG. 7 is a front view of the cap member showing a modification of a proximal-end marker of the medical tube in FIG. 1.

Note that, regarding the distal-end marker 12 and the proximal-end marker 13 of the medical tube 1 according to this embodiment, this description of markers is non-limiting and other markers may be included. As one non-limiting example, as shown in FIGS. 6 and 7, identification information for identifying the second lumen 5a, for example, a serial number, may be employed as the distal-end marker 12 and the proximal-end marker 13.

In this case, from among the serial numbers indicated on the inner surface of the first lumen 4 in the image P acquired by using the endoscope 6, the operator can read the serial number (for example, "6") of the position at which the operator wants to make the treatment tool 7 protrude, and, by inserting the treatment tool 7 via the peripheral through-hole 9a for which the corresponding serial number (for example, "6") is provided on the cap member 3, the operator can make the treatment tool 7 protrude at the desired position. In other words, with such serial numbers, there is an advantage in that the operator can directly ascertain the position at which the treatment tool 7 should be inserted on the basis of the serial number the operator has read in the image P acquired by using the endoscope 6.

In this embodiment, although an example in which the second lumens 5 and 5*a* are collapsed and expanded when the treatment tool 7 is inserted has been described, there is no limitation thereto, and second lumens 5 and 5*a* that are not collapsed may be employed.

Although an example in which the cap member 3 is attached in order to facilitate insertion of the treatment tool 7 into one of the second lumens 5 and 5*a* has been described, there is no limitation thereto, and the cap member 3 may be omitted. In that case, the proximal-end marker 13 may be provided at the proximal-end portion of the tube main body 2.

Next, a medical system according to an embodiment of the present invention will be described below with reference to the drawings.

In describing this embodiment, the same reference signs are assigned to portions that have common configurations with those of the medical tube 1 according to the above-described embodiment, and descriptions thereof will be omitted.

Figure 8:
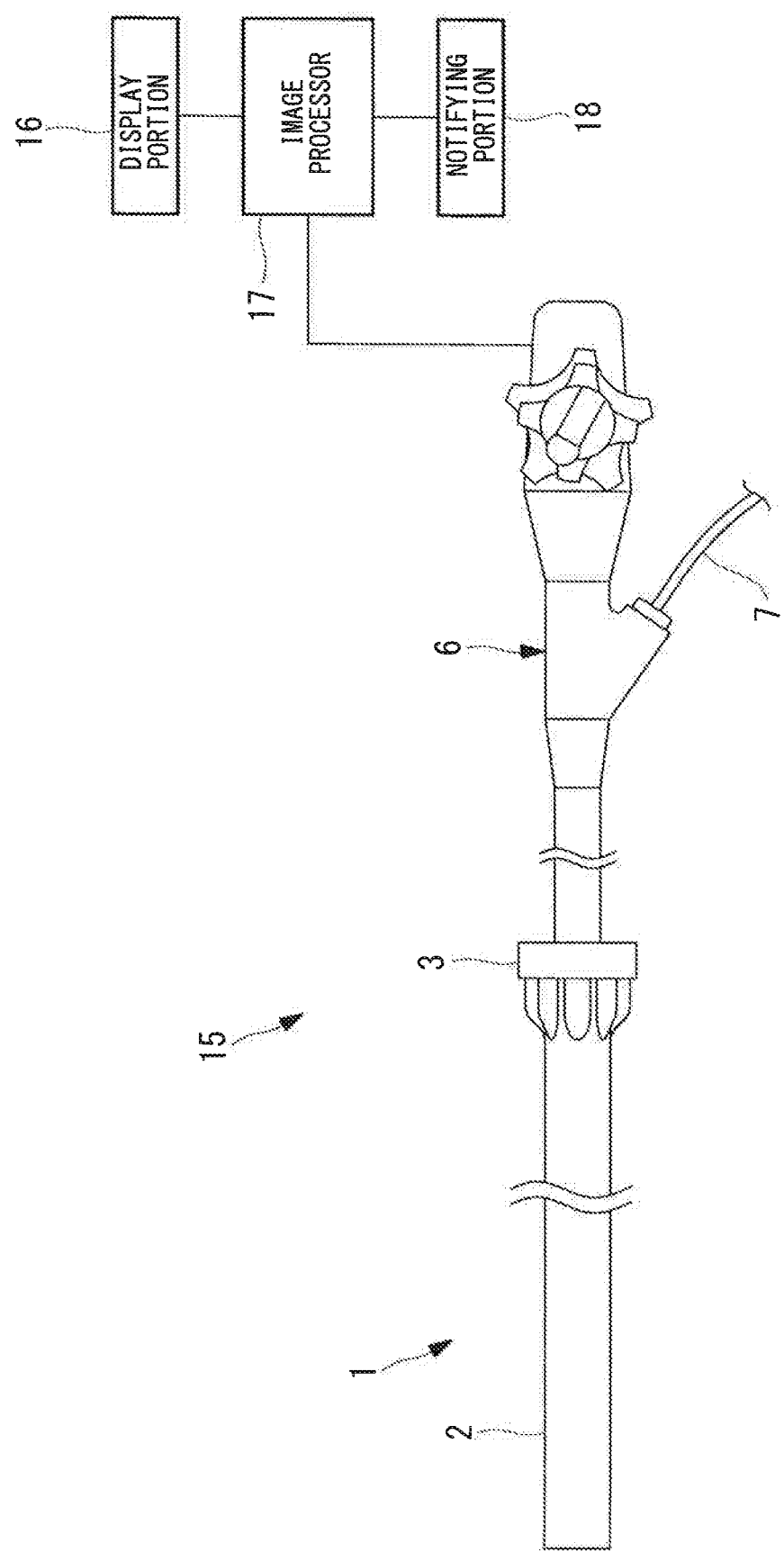
FIG. 8 is an overall configuration diagram showing a medical system according to an embodiment of the present invention.

As shown in FIG. 8, a medical system 15 according to this embodiment is provided with: the medical tube 1; the endoscope 6 inserted into the first lumen 4 of the medical tube 1; a display 16 that is configured to display the image P acquired by using the endoscope 6; an image processor 17 that recognizes the distal-end marker 12 in the acquired image P; and a notifying portion 18 that issues a notification about the identification information of the second lumen 5 on the basis of the distal-end marker 12 recognized by the image processor 17.

Although the medical tube 1 has a structure similar to that of the above-described embodiment, in this embodiment as the distal-end marker 12, a straight-line marker is drawn on the inner surface of the first lumen 4 along a distance in the axial direction, as shown in FIG. 1, and, as the proximal-end marker 13, a set of identification information for identifying the individual second lumens 5 and 5*a*, for example, serial numbers, are included in the vicinity of the individual peripheral through-holes 9 and 9*a* of the cap member 3, as shown in FIG. 7.

As shown in FIG. 5, the image processor 17 is configured so as to recognize an angle θ of the distal-end marker 12 in the image P acquired by using the endoscope 6.

Figure 9:
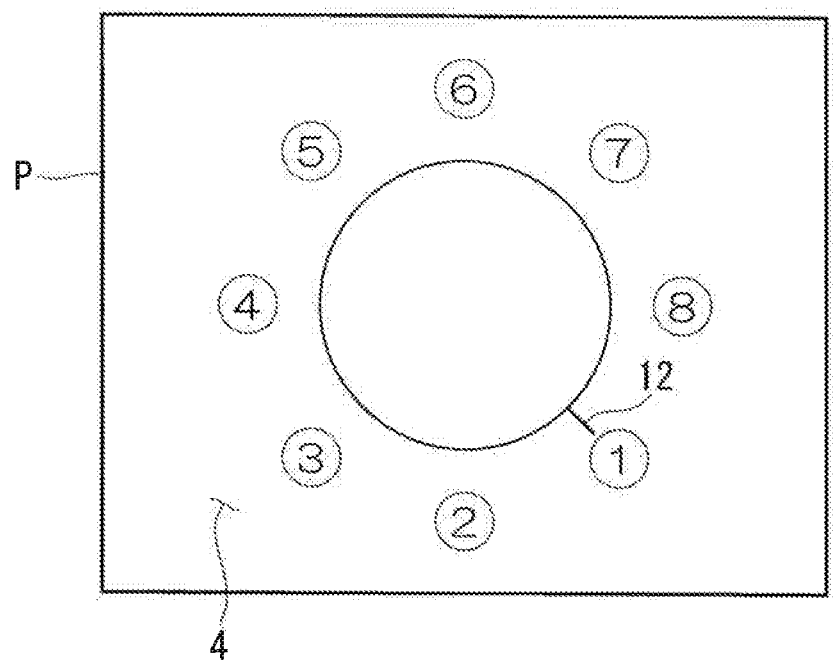
FIG. 9 is a diagram showing an example of an image that includes the numbers assigned to all second lumens about which a notification is issued by a notifying portion of the medical system in FIG. 8.

Then, the notifying portion 18 displays the serial numbers of the second lumens 5 and 5*a* on the display 16 by superimposing them on the endoscope image P, as shown in FIG. 9, on the basis of the angle θ of the distal-end marker 12 recognized by the image processor 17.

For example, in the case in which the distal-end marker 12 is provided at a position aligned with the second lumen 5 having the serial number "1" and, as shown in FIG. 9, the serial numbers at the proximal-end marker 13 are assigned to the individual second lumens 5 and 5*a* clockwise when facing forward, the notifying portion 18 may display "1" in the vicinity of the recognized distal-end marker 12, as shown in FIG. 9, and may display as many serial numbers as there are the second lumens 5 and 5*a* clockwise centered on the image center with substantially equal intervals therebetween.

By doing so, the operator can check the peripheral through-hole 9*a* into which the treatment tool 7 should be inserted on the basis of the serial number displayed on the image P. Thus, even if the medical tube 1 is distorted with respect to the endoscope 6, it is possible to make the treatment tool 7 protrude at the desired position in the image P and to perform treatment just by inserting the treatment tool 7 into the checked peripheral through-hole 9*a*.

Figure 10:
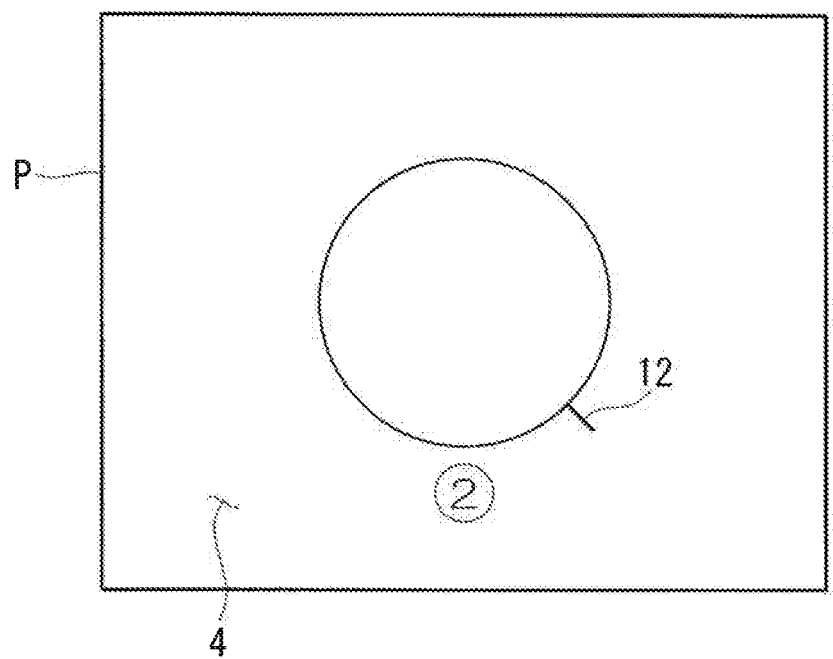
FIG. 10 is a diagram showing an example of an image that includes the number assigned to the second lumen into which the treatment tool should be inserted, about which a notification is issued by the notifying portion of the medical system in FIG. 8.

Note that, in the case in which the position in the image P at which the treatment tool 7 should be made to protrude is set in advance, instead of displaying the serial numbers corresponding to all of the second lumens 5 and 5*a* in the image P, the notifying portion 18 may issue a notification about only the serial number (for example, "2") of the second lumen 5*a* into which the treatment tool 7 should be inserted, as shown in FIG. 10. In addition to the case in which a notification is issued about a single serial number, a notification may be issued about serial numbers of two or more second lumens 5*a*.

For example, in the case in which the treatment tool 7 is a manipulator of an isomorphic master-slave system, the serial numbers of the optimal second lumens 5*a* may be selected so that the positional relationship between the operator and a manipulating portion (not shown) becomes equal to the positional relationship between the endoscope 6 and the distal-end portion of the treatment tool 7.

Figure 11:
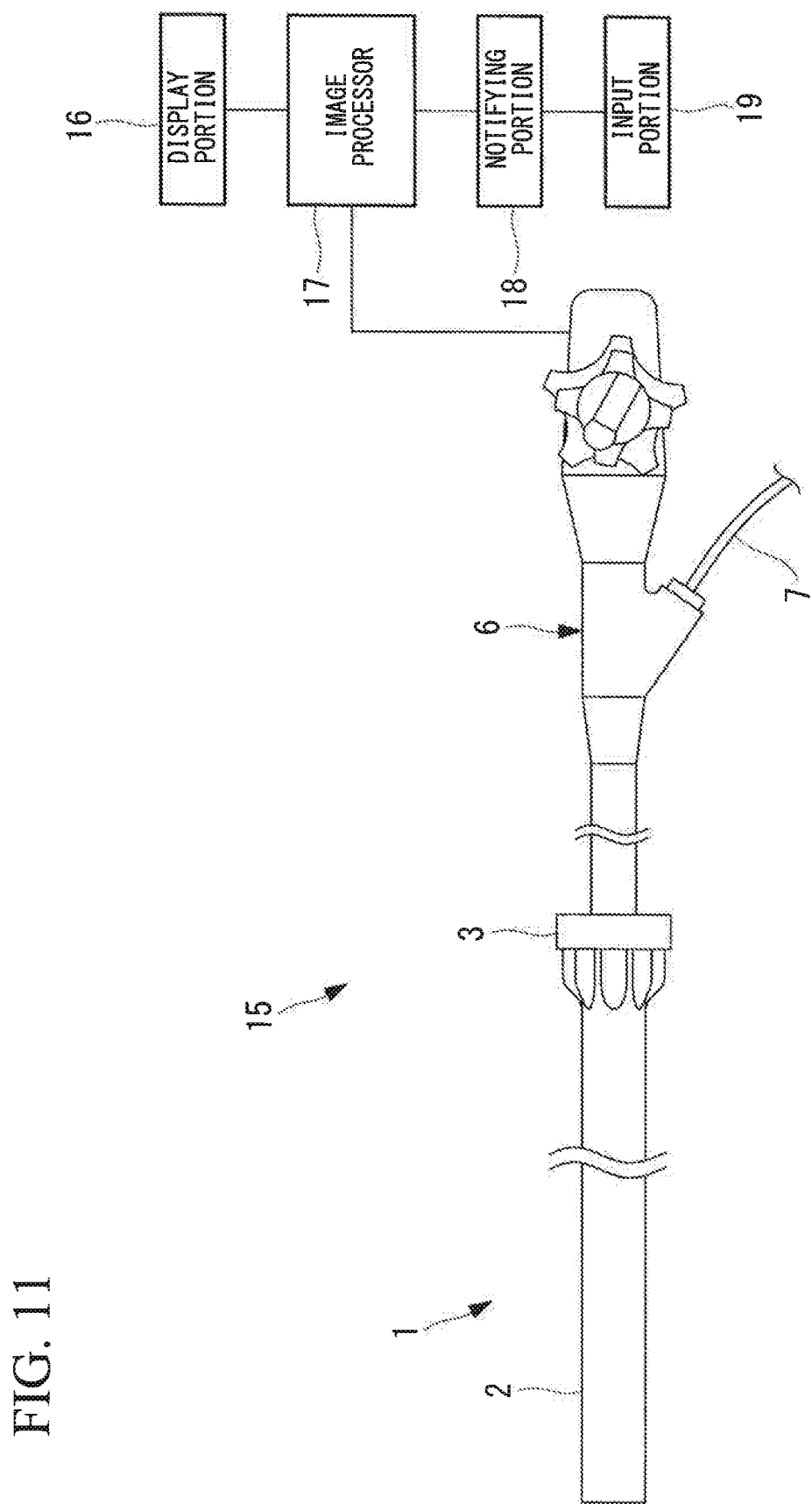
FIG. 11 is an overall configuration diagram showing a modification of the medical system in FIG. 8.

In the case in which there are multiple types of treatment tools 7 to be inserted, and the optimal protruding positions in the image P differ in accordance with the treatment tools 7, an input 19 with which input about the types of the treatment tools 7 is made may be provided, as shown in FIG. 11.

In other words, on the basis of the angle θ of the distal-end marker 12 recognized by the image processor 17 and in accordance with the type of the treatment tool 7 input via the input 19, the notifying portion 18 may set and issue a notification about the peripheral through-hole 9*a* through which the treatment tool 7 should be inserted.

For example, in the case in which the treatment tool 7 is a lesion-raising gripping forceps, the treatment tool 7 can be protruded at a position away from the lesion. In this case, the position of the lesion may be specified by means of image recognition, alternatively, by allowing the operator to specify the position in the image P, and thus, the second lumen 5*a* at a position that is the farthest from said lesion may be selected.

In the case in which the treatment tool 7 is a jointless treatment tool, because the lesion needs to be in the vicinity of a position extended straight from the distal-end of the opening 14 of the medical tube 1, the second lumen 5*a* that satisfies such conditions may be selected.

In the case in which another treatment tool 7 is in use, the serial numbers of the second lumens 5 and 5*a* may be set so that the treatment tool 7 that is newly inserted does not interfere with the treatment tool 7 in use. Examples of such cases include cases in which the need to insert a new treatment tool 7 unexpectedly arises, such as when bleeding occurs, when performing an additional local injection, or the like.

In this embodiment, although the notifying portion 18 displays the serial numbers for identifying the second lumens 5 and 5*a* on the display 16 together with the image P, alternatively, light sources such as LEDs or the like may be provided in the cap member 3 at positions corresponding to the individual second lumens 5 and 5*a*, and a notification may be issued by causing an LED corresponding to the selected second lumen 5*a* to emit light. In addition, shutters that open and close the individual peripheral through-holes 9 and 9*a* may be provided, and a notification may be issued by opening only the shutter of the peripheral through-hole 9*a* corresponding to the selected second lumen 5*a*.

As a result, the above-described embodiment leads to the following aspects.

An aspect of the present invention is a medical system comprising: a medical tube, the medical tube comprising: a main body; a first lumen formed in the main body in a longitudinal direction of the main body; a plurality of second lumens formed in the main body in the longitudinal direction of the main body, the plurality of second lumens formed about at least a portion of a circumference of the first lumen; a portion of a distal end of the first lumen comprising a first indicator; the first indicator configured to specify a rotational direction position about the longitudinal direction of the main body of any one of the plurality of second lumens with respect to the first lumen; and a portion of the proximal end of the main body comprising a plurality of second indicators, wherein each of the plurality of second indicators are configured to indicate each of the plurality of second lumens specified by the first indicator; and an endoscope; a display configured to display an image; and one or more processors, the processors configured to: receive an image data from the endoscope; generate first information in regards to the second indicator specified by the first indicator recognized in the image data; transmit the first information to the display.

The above-described aspect may be provided with the first indicator has identification information corresponding to each of the plurality of second indicators, wherein the first information comprises the identification information.

The above-described aspect may be provided with the one or more processors are configured to: receive second information about a treatment tool to be used; determine one or more second lumens which are suitable to be used by the treatment tool on the basis of the second information; wherein the first information include the identification information of the determined one or more second lumens.

Another aspect of the present invention is a medical system comprising: a medical tube, the medical tube comprising: a main body; a first lumen formed in the main body in a longitudinal direction of the main body; a plurality of second lumens formed in the main body in the longitudinal direction of the main body, the plurality of second lumens formed about at least a portion of a circumference of the first lumen; a portion of a distal end of the first lumen comprising a first indicator; the first indicator configured to specify a rotational direction position about the longitudinal direction of the main body of any one of the plurality of second lumens with respect to the first lumen; a cap configured to attach to a proximal end of the main body; and a proximal portion of the cap, the proximal portion comprising a plurality of second indicators, each of the plurality of second indicators configured to indicate each of the plurality of second lumens specified by the first indicator; and an endoscope; a display configured to display an image; one or more processors, the processors configured to: receive an image data from the endoscope; generate first information in regards to the second indicator specified by the first indicator recognized in the image data; send the first information to the display.

The above-described aspect may be provided with the first indicator has identification information corresponding to each of the plurality of second indicators, wherein the first information comprises the identification information.

The above-described aspect may be provided with the processors configured to: receive second information about a treatment tool to be used; determine one or more second lumens which are suitable to be used by the treatment tool on the basis of the second information; wherein the first information include the identification information of the determined one or more second lumens.

REFERENCE SIGNS LIST 1 medical tube
2 tube main body
3 cap member
4 first lumen
5, 5a second lumen
6 endoscope
7 treatment tool
8 center through-hole
9, 9a peripheral through-hole (proximal-end opening)
10 insertion cylindrical portion
11 proximal-end opening
12 distal-end marker (first indicator)
13 proximal-end marker (second indicator)
14 distal-end opening
15 medical system
16 display
17 image processor
18 notifying portion
19 input
P image

The invention claimed is:

1. A medical tube comprising:
   a main body;
   a first lumen formed in the main body in a longitudinal direction of the main body;
   a plurality of second lumens formed in the main body in the longitudinal direction of the main body, the plurality of second lumens formed about at least a portion of a circumference of the first lumen;
   a portion of a distal end of the first lumen comprising a first marker, the first marker configured to specify a rotational direction position about the longitudinal direction of the main body of any one of the plurality of second lumens with respect to the first lumen; and
   a portion of the proximal end of the main body comprising a second marker, wherein the second marker is configured to indicate one of the plurality of second lumens specified by the first marker.

2. A medical tube according to claim 1,
   wherein the second marker comprises a plurality of second markers, and wherein each of the plurality of second markers are configured to indicate each of the plurality of second lumens specified by the first marker.

3. A medical tube according to claim 2,
   wherein the first marker has identification information corresponding to each of the plurality of second markers, wherein the plurality of second markers correspond to each of the plurality of second lumens.

4. A medical tube according to claim 1, further comprising:
   a cap configured to attach to a proximal end of the main body,
   a proximal portion of the cap, the proximal portion comprising a plurality of second markers, each of the plurality of second markers configured to indicate each of the plurality of second lumens specified by the first marker.

5. A medical tube according to claim 4, wherein the cap comprises:

a hollow cylinder configured to receive a treatment tool inserted therethrough, wherein the second lumen is configured to receive the hollow cylinder inserted therethrough.

6. A medical tube according to claim 1,
wherein an inner diameter of each of the plurality of second lumens is configured to expand to a diameter of an outer diameter of a treatment tool.

7. A medical tube comprising:
a main body;
- a first lumen formed in the main body in a longitudinal direction of the main body;
- a plurality of second lumens formed in the main body in the longitudinal direction of the main body, the plurality of second lumens formed about at least a portion of a circumference of the first lumen;
- a portion of a distal end of the first lumen comprising a first marker;

the first marker configured to specify a rotational direction position about the longitudinal direction of the main body of any one of the plurality of second lumens with respect to the first lumen;
a cap configured to attach to a proximal end of the main body; and
- a proximal portion of the cap, the proximal portion comprising a plurality of second markers, each of the plurality of second markers configured to indicate each of the plurality of second lumens specified by the first marker.

8. A medical tube according to claim 7,
wherein an inner diameter of each of the plurality of second lumens is configured to expand to a diameter of an outer diameter of a treatment tool.

9. A medical tube according to claim 7,
wherein the first marker has identification information corresponding to each of the plurality of second markers, wherein the plurality of second markers correspond to each of the plurality of second lumens.

10. A medical tube according to claim 7, wherein the cap comprises:
a hollow cylinder configured to receive a treatment tool inserted therethrough, wherein the second lumen is configured to receive the hollow cylinder inserted therethrough.

11. A medical tube according to claim 7, further comprising a portion of the proximal end of the main body comprising the plurality of second markers, wherein each of the plurality of second markers are configured to indicate each of the plurality of second lumens specified by the first marker.

* * * * *